United States Patent [19]

Cushman

[11] 4,228,356
[45] Oct. 14, 1980

[54] OPTIMUM CONTRAST PANORAMIC DENTAL RADIOGRAPHY AND METHODS OF PROVIDING THEREFOR

[75] Inventor: Robert H. Cushman, Princeton, N.J.

[73] Assignee: Pennwalt Corporation, Philadelphia, Pa.

[21] Appl. No.: 939,646

[22] Filed: Sep. 1, 1978

[51] Int. Cl.³ .................. G03B 41/16; A61B 6/14; H01J 31/50
[52] U.S. Cl. .................. 250/439 P; 250/213 VT
[58] Field of Search ............. 250/439 P, 213 VT, 480

[56] References Cited

U.S. PATENT DOCUMENTS

| 2,798,958 | 7/1957 | Hudson et al. | 250/439 P |
| 3,666,957 | 5/1972 | Wyess | 250/213 VT |
| 3,681,606 | 8/1972 | Tinney | 250/213 VT |

OTHER PUBLICATIONS

Yin et al., "The Lixiscope: A Pocket-Size X-Ray Imaging System", *NASA Technical Memorandum 78064*, Jan. 1978.
Owen, L. D., "The Channeltron Electron Multiplier Array and Its Application to Low-Level Detection Devices", IPC Science and Technology Press Ltd., Sep. 1972, as reprinted by Galileo Electro-Optics Corp., Galileo Park, Sturbridge, Mass.

*Primary Examiner*—Alfred E. Smith
*Assistant Examiner*—T. N. Grigsby

[57] ABSTRACT

Panoramic dental X-ray machine includes a tubehead-camera assembly which employs, in its simplest embodiment, three vertically stacked image intensifiers, the totality of their radiation input faces being substantially similar in shape and dimensions to a slot in a front panel of the camera assembly, the input faces being secured against the slot and aligned therewith such that radiations passing therethrough must then pass through the image intensifiers. Means for selectively controllably varying the potential across each of the individual image intensifiers varies the electron gain of that image intensifier to thus provide optimal contrast between multi-density structures of the dental arch and surrounding areas on a full size radiograph.

8 Claims, 5 Drawing Figures

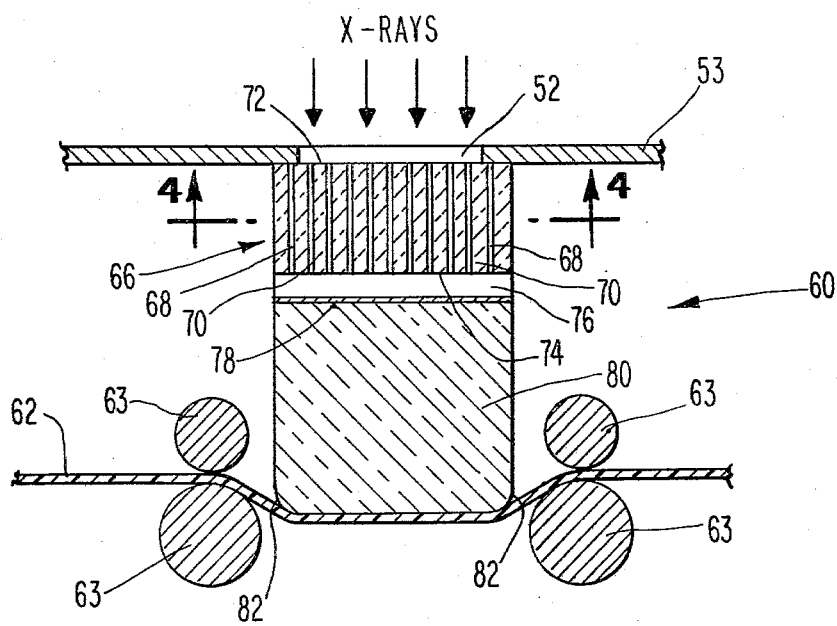
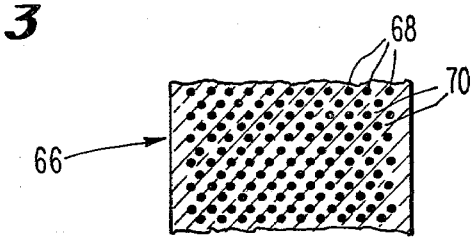
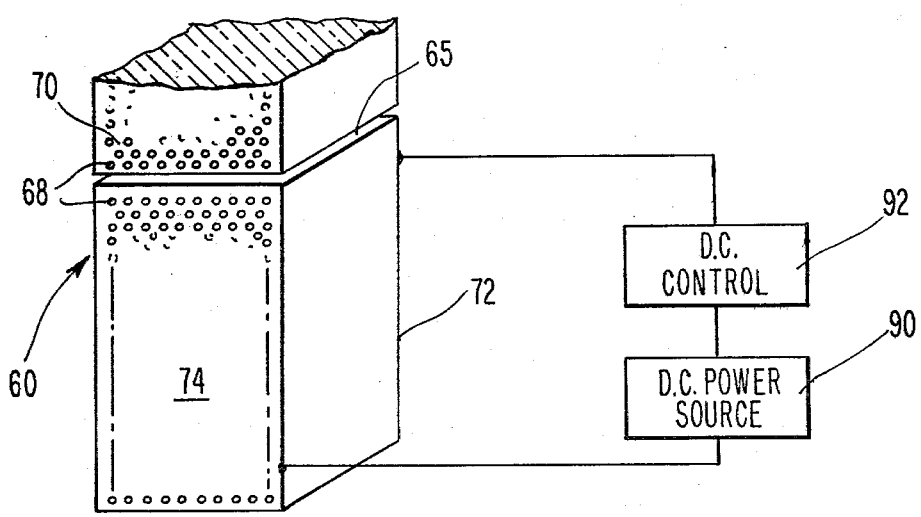

OPTIMUM CONTRAST PANORAMIC DENTAL RADIOGRAPHY AND METHODS OF PROVIDING THEREFOR

STATEMENT OF THE INVENTION

This invention relates to X-ray machines and more particularly concerns means for optimizing contrast among multidensity structures associated with the dental arch area on a panoramic radiograph.

CROSS-REFERENCE TO RELATED APPLICATIONS

Reference is hereby made to copending patent application of Robert H. Cushman for "Panoramic Dental X-Ray Machine Employing Image Intensifying Means", Ser. No. 053,127, filed July 20, 1978, assigned to the present assignee.

BACKGROUND OF THE INVENTION

Prior art panoramic dental X-ray machines are well known. Some provide a continuous image of the dental arch area and commonly employ an X-ray source and X-ray film both optically aligned with each other and supported on a rotatable carrying arm which orbits a patient situated in the path of the X-ray beams. The patient may remain stationary or be transported in a patient chair in accordance with various type drive mechanisms in order to simulate the generally elliptical shape of the human dental arch. The continuous image radiograph provides the dentist with a panoramic view of the teeth and associated structures and is therefore a useful diagnostic aid in many phases of dental practice.

Various other prior art apparatus provide a discontinuous, or split image panoramic radiograph which possesses certain advantages. Here, the dentist is presented with additional interpretive information since two distinctly different views of the incisors, or centrals area are provided. Additionally, overlying spinal shadows which would be cast over the central-bicuspid region are eliminated since X-rays are not generated when the spine is aligned with the X-ray source and film.

Regardless of the type radiographic image to be obtained, i.e., continuous or discontinuous, compensation is usually made for the fact that the curvature of the desired area of focus is generally not a true circle or ellipse. Thus, the rate of film travel must be varied in accordance with the rate of travel of the X-ray source about the patient's head in order that the radiological projections occupy a distance on the film equal to the linear distance of a curved structure being X-rayed, such as a typical dental arch.

In U.S. Pat. No. 2,798,958, apparatus is disclosed for varying the rate of film travel relative to the rate of travel of the X-ray source. The X-ray source and film carrier are both supported by a single member permitting both the X-ray source and film carrier to orbit the patient at an uniform rate of travel. Means are also disclosed for reorienting the patient after completion of one-half of the excursion cycle in order to relocate the center of the axis of rotation with respect to the patient's head prior to X-raying the other one-half of the dental arch in order to provide the discontinuous, or split radiographic images.

In U.S. Pat. No. 3,045,118, issued 1962 to Hollman et al., apparatus is disclosed which automatically shifts the patient in order that the line of sight between the X-ray source and film bypasses the patient's spinal column and permits X-raying of the other half of the dental arch. Apparatus is also disclosed therein for continuous moving an X-ray source and extra-oral film holder about the patient.

In U.S. Pat. No. 3,636,349, issued 1972 to Faude et al., assigned to the present assignee, structure is disclosed for revolving an X-ray source and film carrier about the head of a patient who remains fixed in position while the centerline of the orbit continuously moves through an arcuate path approximating the arch of the patient's teeth. The patent further discloses film carrier means which may be used advantageously in the practice of the present invention.

Thus, the prior art discloses various types of structure, apparatus and mechanisms for orbiting the X-ray source-X-ray film (tubehead-camera) assemblies in circular or arcuate paths; for varying film travel speed in accordance with tubehead-camera assembly movements; for shifting the patient in a chair; and for providing continuous or discontinuous type radiographic images.

Attempts have recently been made to employ image intensification devices in conjunction with associated electronic peripheral components and equipment to substantially lessen the overall radiation dosages to which a patient is subjected without any concomitant sacrifice in contrast, resolution, or physical dimensions of the final radiograph. It is appreciated that radiographs of adequate physical dimensions, i.e., about 5"×12", are considered necessary if meaningful information therefrom is to be consistently obtained by a dentist. Such full size radiographs generally required the presence of cathode ray tubes, electronic amplifiers and sweeps, synchronous circuits, and the like.

SUMMARY OF THE INVENTION

The present invention may be used advantageously with the structures, apparatus, and mechanisms described in the above discussed U.S. patents, or may be readily adpated thereto by one skilled in the art. In its simplest embodiment, the present invention proposes means whereby radiations passing through structures associated with dental arch areas are directed substantially simultaneously into three adjacent, vertically aligned image intensifying devices having radiation input faces which oppose the narrow slot in the front panel of the camera assembly (film holder assembly) which carries the light-sensitive film to be activated by photons exiting output faces of the individual image intensifiers. The image intensifiers are secured within the camera assembly against the slot in optical alignment therewith.

The present invention also contemplates a plurality of horizontally and vertically disposed matrices of miniature image intensifying devices wherein each is capable of having its electron gain individually controlled to thus yield still a more precise contrast. Such matrices may be considered an obvious extension of the teachings of the present invention.

The light-sensitive film may press delicately against the output faces of the three image intensifying devices or be disposed in very close spaced relationship thereto as the film travels in accordance with a controlled rate of speed dictated by the type of image desired, as described in the aforementioned patents or cross-referenced copending application, or by the shape of focal trough desired. Film travel speed may, of course, be made to accurately follow a predetermined speed versus location relationship to provide the desired focal trough shape.

Thus, the present invention is capable of providing full size radiographs, i.e., about 5"×12", wherein contrast among the dental arch structures of varying densities can readily be controlled to yield increased diagnostic information to a dentist. The present invention provides significant reduction in X-ray beam intensities with an accompanying dose reduction of radiation to the patient, and requires no large and expensive image intensifiers or associated auxiliary electronic equipment to produce the full size radiographs. The lesser amount of power required by the X-ray tubehead enables the size and cost of the tubehead power supply to be substantially reduced.

BRIEF DESCRIPTION OF THE DRAWINGS

FIG. 3 is a sectional view of an image intensifying device of FIG. 2 taken along line 3—3 thereof.

FIG. 4 is a section of the microchannel plate of the image intensifying device of FIG. 3 taken along line 4—4 thereof.

FIG. 5 is a diagrammatic perspective view of the image intensifying devices of FIG. 2 illustrating means for applying specified potentials thereto.

DETAILED DESCRIPTION OF THE INVENTION

Figures 1, 2:
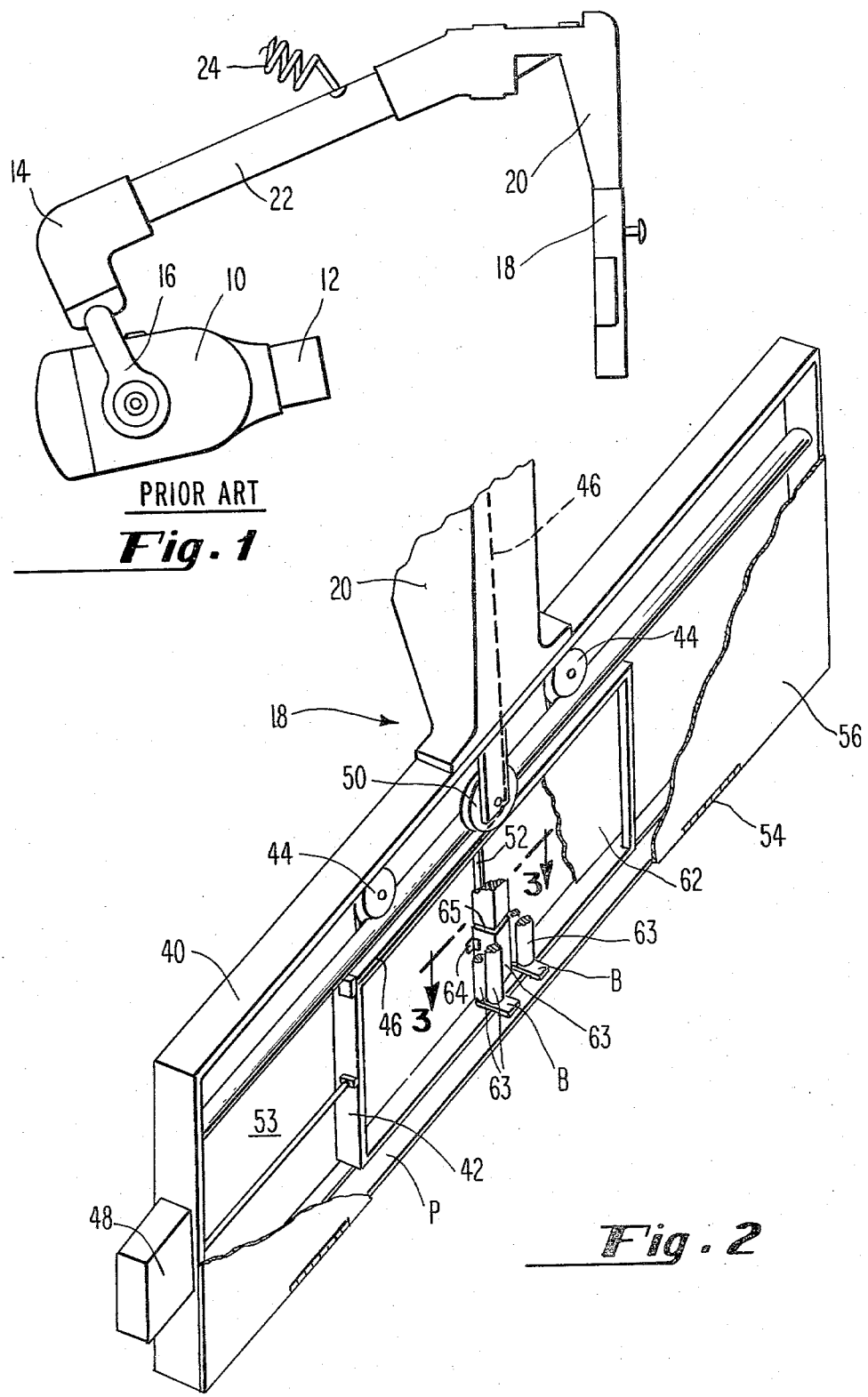
FIG. 1 is an assembly view of a prior art tubehead-camera assembly of a dental X-ray machine.
FIG. 2 is a perspective view of the camera (film holder) assembly of FIG. 1 including a plurality of vertically aligned image intensifying devices positioned for use therewith.

In FIG. 1, tubehead 10 includes cone 12 which focuses X-rays generated by an X-ray source or tube within the tubehead. Trunnion 14 carries yoke 16 which permits limited tubehead rotation. A camera or film holder assembly 18 contains X-ray film to be activated by the X-ray source. Film holder assembly 18 is supported by a film holder assembly support 20 which receives one end of horizontal arm 22, its other end received by trunnion 14. Horizontal arm 22 and film holder assembly support 20 maintain tubehead 10 and film holder assembly 18 a specified distance from each other and in alignment with the patient's head as tubehead 10 and film holder assembly 18 rotate about the patient. Power is supplied to the X-ray source through cable 24. The entire assembly abovedescribed is supported by an assembly support arm (not shown) which additionally supports a suitable motor (also not shown) for rotating the tubehead and camera assembly as a unit.

Film holder assembly 18 is conventional, except as modified, later described. It comprises film holder 40 (FIG. 2), film carriage 42 which travels within the film holder assembly along rollers 44 when cable 46 and retrieving spring 48 cooperate, through cable roller 50 and other means, to move film carriage 42 and its film past vertical slit diaphragm or camera slot 52 disposed centrally the front panel 53 of the film holder assembly. Slot 52, of course, permits X-rays from tubehead 10 to pass therethrough for activation of the film. Hinges 54 permit door 56 to be opened for gaining access to the interior of film holder assembly 18. Door 56 is provided with a lead shield (not shown) aligned with tubehead 10 and slot 52.

Cable 46 communicates with suitable structure for controlling the rate of travel of film carriage 42 independently of the speed of rotation of the tubehead-camera assembly. Specific means for controlling rate of film travel speed as well as means for effecting rotation of the tubehead-camera assembly form no part of the present invention. Reference however is again made to the aforementioned U.S. patents for disclosing and teaching such means. Reference is also made to the cross-referenced related patent application.

A plurality of image intensifying devices 60, light-sensitive film 62, and film guide roller assemblies 63 modify the structure of conventional film holder assembly 18. Image intensifiers 60, each in suitable vacuum envelopes, or in a common vacuum envelope, are vertically disposed and are aligned with slot 52 and secured thereagainst within the film holder assembly by suitable means, such as electrically non-conductive brackets 64. The illustrated image intensifiers will have nominal dimensions of 1 5/6"×½"×⅜", the 1 5/6"×⅜" dimensions defining input faces which oppose the nominal 5⅛"×17/64" opening of slot 52 of the camera. Any suitable electrically non-conductive or dielectric film 65 separates each of the image intensifying devices 60.

The bundles of radiation passing through slot 52 strike the input faces 72 of lead glass microchannel plates 66 (FIGS. 3 and 4) comprising arrays of spaced parallel microchannels 68 aligned with the direction of travel of the X-rays. Microchannels 68 are hollow glass cylinders with a known resistive secondary-emission coating disposed on their interior surfaces. Interstices 70, separating the microchannels from each other, comprise a lead glass which converts the X-ray to electrons via bombardment of the lead ions in the glass by the X-rays. The microchannels are electrically connected in parallel by means of a metallic film of chromium disposed on input face 72 and output face 74 of the microchannel plate 66. Alternatively, input face 72 may be coated with a suitable conversion coating to convert the X-rays to electrons. When a potential is applied between these faces, an uniform axial electrostatic field is generated in each of the microchannels. Input faces 72 are electrically insulated from front panel 53 by suitable means. Thus, an electron entering a microchannel adjacent the input end of microchannel plate 66 will be vastly multiplied in number before exiting at output face 74 due to cascading action wherein primary electrons, initially formed by the aforementioned bombardment, collide with the secondary-emission coating material to cause secondary electrons to be emitted. These secondary electrons now assume the role of primary electrons for the next collision further down the microchannel, and so on. It is appreciated that other image intensifying techniques which will convert the X-rays to electrons, multiply them, and then provides an amplified light output may be used advantageously with the present invention.

Typically, each microchannel 68 is about 12 microns in diameter. The microchannels have a center-to-center spacing of about 15 microns. Such microchannel plate 66 is approximately ⅛" in thickness, the length-to-diameter ratio of each microchannel is about 250.

The multiplied electrons leaving output face 74 of each image intensifier 60 are accelerated by varying voltages across a gap 76 of about 0.05". The accelerated electrons are caused to impinge on a phosphor scr___ disposed on the input side of a fiber optic face pl___. Phosphor screen 78 converts the electrons back to photons which are transmitted through fiber optic face plate 80 to thereby activate the film 62. Film 62 comprises a single or double emulsion layer having a conventional backing plate, an emulsion layer facing the image intensifier. Intensifying screens used with conventional X-ray equipment, are not required in the practice of the present invention.

The resultant intensified images may have static and dynamic resolutions exceeding 10 and 7 line pairs/mm respectively. The radiation dosage to the patient is reduced by about 10 to 1. Experiments have confirmed 40 to 1 dosage reductions but with some increase in noise levels. Optimum results for any specific application therefore requires balancing dose reduction and noise. As aforementioned, electron gain, and hence dose reduction, may be achieved by adjusting potential applied to the image intensifiers.

Means are known for providing a sufficient voltage across gap 76 to accelerate the multiplied electrons from microchannel plate 66 to phosphor screen 78 and for vacuum sealing each image intensifying device 60 for proper operation thereof.

In FIG. 5, means for applying the potential across the input and output faces of each image intensifier is diagrammatically illustrated as a D.C. high voltage power source 90. The potential across each image intensifier is controlled by individual control means 92 associated with each power source 90. Control means 92 may be caused to automatically continuously vary the potential across the input and output faces by means of conventional feedback circuits which sense the quantum of radiation striking the film to produce control signals for continuously adjusting the gain for optimal contrast, or the gain may be varied in a predetermined cyclical manner based on data and information derived from previous experiments.

Thus, if it is desired to optimize contrast between high and low density structures, for example, such as the teeth and tissue respectively, the gain of the image intensifier receiving the radiation from the low density structure may be reduced to provide a flatter contrast, as compared to the contrast normally obtained between the two, i.e., a white image of the teeth on an almost black background representing the tissue, tongue, and the like. Similarly, a medium density structure of porous bone, such as the jaw, can be optimally contrasted with either tissue or teeth by simply controlling the gain of the proper image intensifier.

If:

$$\text{Optical Density} = \log \frac{\text{(incident light intensity)}}{\text{(transmitted light intensity)}}$$

then typical optical density values of various structures of the dental arch area are as follows:

| | |
|---|---|
| hard enamels | .02 |
| alveolar ridge | .04 |
| lamina dura | .04 |
| dentin | .8–1.0 |
| nutrient canal | 1.5 |
| soft tissue | 1.7–2.0 |

Soft tissue, having an optical density, or "blackness", of approximately 2.0, provides images on a radiograph wherein only about 1/100 of light impinging directly thereon will pass therethrough (log of 100 equals 2). Thus, the image of soft tissue is normally quite dark. On the other hand, dentin has an optical density of about 1.0. The image of dentin on a radiograph transmits about 1/10 of the light (log of 10 equals 1) and hence, shows up lighter than the soft tissue.

With the abovementioned values assigned to the various components of the image intensifiers, i.e., microchannel length to diameter ratio, gap space, etc., contrast between cheek and teeth on the radiograph may readily be improved, through conventional feedback systems, for example, by decreasing potential across that image intensifier associated with the cheeks, and permitting the potential across that image intensifier associated with the teeth to remain substantially unchanged.

Alternatively, if desired, potential applied between the input and output faces of the microchannel plate of the image intensifier associated with the cheeks may remain unchanged while increasing the potential applied to the microchannel plate of the image intensifier associated with the teeth. Of course, a combination of either procedure may be used.

Contrast may be varied by varying the gain of an image intensifier. The gain of an image intensifier may be increased by increasing the difference in potential applied between its input face and output face. Dose reduction was improved from 10 to 1 to 40 to 1 when the difference in voltages was increased from 480 volts to 730 volts, i.e., when the voltages applied to input face 72 and output face 74 was changed from 5.63 kV and 5.15 kV respectively to 5.83 kV and 5.10 kV respectively.

It is appreciated that more precise control of contrast may be obtained if a greater number of image intensifiers are employed, and it is apparent that such greater number may readily be employed without departing from the spirit and scope of the present invention.

In lieu of conventional feedback systems, a "memory" system may be used which makes use of data already developed with respect to the dental arch area or object being radiographed. Such developed data may then be used to control the gains of the respective image intensifiers in order to optimize or maximize the data. For example, voltages applied to an image intensifier could be controlled by a cam operated potentiometer, or by an appropriately shaped electrical signal created by a non-linear oscillator, or the like. Thus, the memory system is frequently less expensive and simpler to use than the feedback system which requires sensing the effects being received, comparing them to a preset standard, and then fixing the input signal to thereby optimize results.

Image intensifiers 60 have an indicated depth of about ½" which may readily be changed by simply increasing or decreasing the depth of optic face plate 80. The nominal ½" depth of image intensifier 60 is accommodative to the existing film holder assembly 18 without requiring unnecessary modifications thereto. Film guide roller assemblies 63 (FIGS. 2 and 3) permit film 62 to travel unimpeded in constant light contact relationship across the output face of fiber optic face plate 80 in accordance with a rate of speed dictated by the radiographic image desired. Film guide roller assemblies 63 are rotatably mounted on brackets B, secured to bottom plate P of film holder assembly 18. Alternatively, the film guide roller assemblies may be mounted to door 56. Means for adjusting the film guide roller assemblies in order to accommodate image intensifiers of varying depths are also known and are not disclosed or illustrated herein.

Output face of fiber optic face plate 80 is provided with small radii 82 in order to prevent possible damage to film 62 as it lightly slides thereacross. Although film 62 will, ideally, contact the output face of fiber optic face plate 80, photon image scatter is within tolerable limits if distance between film 62 and output face of face plate 80 is maintained less than about 0.005".

It is understood of course that the individual fibers comprising fiber optic face plate 80 are aligned in the same direction as microchannels 68.

It is envisaged that certain structures may require a fiber optic face plate of substantially increased depth. The present inventive device may be used therewith since fiber optic face plates permit an image plane to be transmitted directly to its outer surface without the danger of generating internal reflections.

The invention is not intended to be limited to the image intensifying device shown and described. For example, X-ray detection or image intensifying devices employing scintillators, photocathodes, aluminized phosphor screens, electronic multiplier arrays of various types, etc. may be used advantageously with the present invention, with adaptation. Further, radioisotopic or radioactive sources may be used, and natural radiation from the human body may be useful for static X-ray as well as tomographic applications.

Film holder assembly 18 will be made light tight by conventional means prior to patient radiographing.

It is noted that any artifact produced on the radiograph by dielectric 65, or insulating film, barrier layer, or where the image intensifiers abut one another, is negligible since, if visible at all, will take the form of a straight line which rarely leads to a faulty diagnosis.

An embodiment of the invention constructed in accordance with the principles disclosed herein utilized an X-ray source capable of generating a continuous series of X-ray pulses for producing panoramic radiographs. The X-rays are generated by 50 to 90 kVp applied to a half-wave self-rectified tungsten anode X-ray tube, the incoming X-rays having an input energy ranging between about 20 to 40 keV effective. The sum of the image intensifiers, phosphors, etc. rise times and decay times should typically be less than 760 microseconds in order that target system resolutions will be obtained. Fast, light-sensitive dental film in the neighborhood of ASA 3000 may be used although slower film, approaching ASA 400 also have good results. Phosphor screen 78 must be spectrally matched to the film used to insure optimal activation of the photons. The photons emanating from phosphor screen 78 have a spectral radiance wavelength ranging between about 250–425 nanometers.

Panoramic techniques in current use by the assignee of the present invention employ 50 to 90 kVp at 5 mA for about 20 seconds duration. Panoramic techniques employing the principles of the instant invention require only 50 kVp maximum at 0.5 mA for the same duration. The focal spot of the X-ray tube to film 62 distance is 16.84" nominal.

The invention is not intended to be limited to panoramic dental radiography, since one skilled in the art may readily adapt the principles disclosed herein, for example, to conventional dental and medical X-ray apparatus.

I claim:

1. An x-ray machine comprising an X-ray source adapted to continuously direct radiation through a slot disposed in a front panel of a film holder assembly containing film controllably movable therewithin for sequentially exposing portions thereof to radiation passing through structures of a patient disposed between said X-ray source and film holder assembly to form a full size panoramic radiograph, a plurality of identical image intensifying devices disposed in vertical alignment secured within said film holder assembly in operable alignment with said slot, said image intensifying devices substantially simultaneously converting said radiations passing through said structures of said patient to electrons and multiplying said electrons to form multiplied electrons, means within said image intensifying devices for converting said multiplied electrons to photons to form corresponding photon images, a plurality of control circuits, one each of said control circuits being connected to a different one of said plurality of image intensifying devices to vary intensity of said photon images of said structures of said patient, said film being in near-contacting relationship with output of said plurality of image intensifying devices for continuously receiving said photon images therefrom, said photon images having intensities which vary with varying densities of said structures on said full size radiograph.

2. The X-ray machine of claim 1 wherein said near-contacting relationship represents a distance less than about 0.005".

3. An X-ray machine comprising an X-ray source adapted to continuously direct radiation through a slot disposed in a front panel of a film holder assembly containing film controllably movable therewithin for sequentially exposing portions thereof to radiation passing through structures of a patient disposed between said X-ray source and film holder assembly to form a full size panoramic radiograph, a plurality of identical image intensifying devices disposed in vertical alignment secured within said film holder assembly in operable alignment with said slot, said image intensifying devices substantially simultaneously converting said radiations passing through said structures of said patient to electrons and multiplying said electrons to form multiplied electrons, means within said image intensifying devices for converting said multiplied electrons to photons to form corresponding photon images, a plurality of control circuits, one each of said control circuits being connected to a different one of said plurality of image intensifying devices to vary intensity of said photon images of said structures of said patient, said film being in sliding contact relationship with output of said plurality of image intensifying devices for continuously receiving said photon images therefrom, said photon images having intensities which vary with varying densities of said structures and in accordance with said control circuits to thereby form optimally contrasted images of said structures on said full size radiograph.

4. The machine of claim 3 wherein each of said control circuits employs a feedback circuit to provide a control signal to adjust gain of each of said plurality of image intensifying devices, each of said control signals being responsive to intensity of selected photon images striking said film.

5. The machine of claim 3 wherein each of said control circuits employs a device which uses data previously developed for said structures to provide a control signal to adjust gain of each of said plurality of image intensifying devices, each of said control signals being responsive to intensity of selected photon images striking said film.

6. In a panoramic dental X-ray machine for providing full size continuous and discontinuous type radiographs of dental arch areas of a patient seated in a chair adapted for movement in accordance with type radiograph to be obtained, said X-ray machine comprising a. an X-ray source, and b. a film holder assembly for holding film to be activated by said source, said film holder assembly having a slot in a front panel thereof to permit radiation from said X-ray source passing through said dental arch area of said patient to pass therethrough, said X-ray machine including means to power said X-ray source and means for controllably continuously moving said film in said film holder assembly past said slot, and other means for orbiting said X-ray source and film holder assembly about said dental arch area of said patient, the combination therewith of the improvement thereto comprising a plurality of identical image intensifying devices having total input face dimensions at least as large as dimensions of said slot, said image intensifying devices being vertically aligned and in operable alignment with said slot, said plurality of identical image intensifying devices converting said radiations passing through said dental arch area and said slot to photon images, control means electrically connected to each of said plurality of identical image intensifying devices for selectively varying intensity of said photon images to provide optimum contrast of varying density structures associated with said dental arch area, said film being in sliding contact relationship with output of said plurality of image intensifying devices for continuously receiving said photon images therefrom, said photon images having intensities which vary with varying densities of said structures and in accordance with said control means to thereby form optimally contrasted images of said structures on said full size radiograph.

7. In a panoramic dental X-ray machine for providing full size continuous and discontinuous type radiographs of dental arch areas of a patient seated in a chair adapted for movement in accordance with type radiograph to be obtained, said X-ray machine comprising a. an X-ray source, and b. a film holder assembly for holding film to be activated by said source, said film holder assembly having a slot in a front panel thereof to permit radiation from said X-ray source passing through said dental arch area of said patient to pass therethrough, said X-ray machine including means to power said X-ray source and means for controllably continuously moving said film in said film holder assembly past said slot, and other means for orbiting said X-ray source and film holder assembly about said dental arch area of said patient, the combination therewith of the improvement thereto comprising a plurality of identical image intensifying devices having total input face dimensions at least as large as dimensions of said slot, said image intensifying devices being vertically aligned and in operable alignment with said slot, said plurality of identical image intensifying devices converting said radiations passing through said dental arch area and said slot to photon images, control means electrically connected to each of said plurality of identical image intensifying devices for selectively varying intensity of said photon images to provide optimum contrast of varying density structures associated with said dental arch area, said film being in near-contacting relationship with output of said plurality of image intensifying devices for continuously receiving said photon images therefrom, said photon images having intensities which vary with varying densities of said structures and in accordance with said control means to thereby form optimally contrasted images of said structures on said full size radiograph.

8. The X-ray machine of claim 7 wherein said near-contact relationship represents a distance less than about 0.005".

* * * * *